(12) United States Patent
Schmieding et al.

(10) Patent No.: US 9,146,576 B2
(45) Date of Patent: Sep. 29, 2015

(54) ARTHROSCOPE ROTATION MECHANISMS AND METHODS OF ENDOSCOPIC ROTATION

(71) Applicant: Arthrex, Inc., Naples, FL (US)

(72) Inventors: Reinhold Schmieding, Naples, FL (US); Craig Speier, Santa Barbara, CA (US); Martin A. Frith, Goleta, CA (US); Sabine Pauli, Seitingen-Oberflacht (DE); Daniel Seeh, Immendingen (DE)

(73) Assignee: ARTHREX, INC., Naples, FL (US)

( * ) Notice: Subject to any disclaimer, the term of this patent is extended or adjusted under 35 U.S.C. 154(b) by 4 days.

(21) Appl. No.: 13/751,725

(22) Filed: Jan. 28, 2013

(65) Prior Publication Data

US 2013/0205936 A1 Aug. 15, 2013

Related U.S. Application Data

(60) Provisional application No. 61/595,389, filed on Feb. 6, 2012.

(51) Int. Cl.
*A61B 1/04* (2006.01)
*G05G 1/10* (2006.01)
*A61B 1/00* (2006.01)
*A61B 1/317* (2006.01)

(52) U.S. Cl.
CPC .............. *G05G 1/10* (2013.01); *A61B 1/00066* (2013.01); *A61B 1/317* (2013.01); *Y10T 74/20474* (2015.01)

(58) Field of Classification Search
None
See application file for complete search history.

(56) References Cited

U.S. PATENT DOCUMENTS

| | | | | |
|---|---|---|---|---|
| 4,779,612 A * | 10/1988 | Kishi | | 600/141 |
| 5,066,295 A * | 11/1991 | Kozak et al. | | 606/47 |
| 5,088,819 A * | 2/1992 | Storz | | 356/241.1 |
| 5,184,602 A * | 2/1993 | Anapliotis et al. | | 600/137 |
| 5,577,654 A * | 11/1996 | Bishop | | 227/175.1 |
| 5,695,448 A * | 12/1997 | Kimura et al. | | 600/121 |
| 5,921,956 A * | 7/1999 | Grinberg et al. | | 604/95.01 |
| 5,984,937 A | 11/1999 | Morse et al. | | |
| 6,221,007 B1 * | 4/2001 | Green | | 600/160 |
| 6,346,076 B1 * | 2/2002 | Rovegno | | 600/173 |
| 6,387,044 B1 * | 5/2002 | Tachibana et al. | | 600/121 |
| 6,500,115 B2 * | 12/2002 | Krattiger et al. | | 600/173 |
| 6,679,874 B2 * | 1/2004 | Miser | | 606/1 |
| 6,692,431 B2 * | 2/2004 | Kazakevich | | 600/178 |
| 7,846,087 B2 | 12/2010 | Stefanchik et al. | | |
| 7,931,624 B2 * | 4/2011 | Smith et al. | | 604/167.06 |
| 8,647,262 B2 * | 2/2014 | Seifert | | 600/146 |
| 2005/0272975 A1 * | 12/2005 | McWeeney et al. | | 600/113 |
| 2007/0249899 A1 * | 10/2007 | Seifert | | 600/109 |
| 2010/0030031 A1 * | 2/2010 | Goldfarb et al. | | 600/163 |
| 2011/0018988 A1 * | 1/2011 | Kazakevich et al. | | 348/68 |
| 2012/0029354 A1 * | 2/2012 | Mark et al. | | 600/439 |
| 2013/0006055 A1 * | 1/2013 | Goldfarb et al. | | 600/137 |
| 2013/0137920 A1 * | 5/2013 | Schaeffer et al. | | 600/104 |

\* cited by examiner

*Primary Examiner* — Matthew J Kasztejna
(74) *Attorney, Agent, or Firm* — Karish & Bjorgum, PC (57) ABSTRACT

A rotation mechanism (rotating device) that can be easily accessed by the surgeon's finger to rotate an endoscope or similar instrument. The rotation mechanism is a device/component with a "starfish" configuration, which can be attached to the endoscope/arthroscope just distal to the eyepiece (or to an alternate attachment to a camera). The starfish component has a plurality of projections that extend radially from the endoscope axis, and beyond the diameter of the mechanism on the camera head that grasps the arthroscope eyecup. The projections can be easily accessed by the surgeon's finger to rotate the endoscope.

5 Claims, 13 Drawing Sheets

SECTION D-D
FIG. 5(g)

SECTION A-A
FIG. 5(f)

SECTION C-C
FIG. 5(e)

SECTION D-D
FIG. 6(g)

SECTION A-A
FIG. 6(f)

SECTION E-E
FIG. 6(e)

ARTHROSCOPE ROTATION MECHANISMS AND METHODS OF ENDOSCOPIC ROTATION

CROSS-REFERENCE TO RELATED APPLICATIONS

This application claims the benefit of U.S. Provisional Application No. 61/595,389 filed Feb. 6, 2012, the disclosure of which is incorporated by reference in its entirety herein.

FIELD OF THE INVENTION

The present invention relates to endoscopes (scopes) used in surgery and, more particularly, to endoscopes or similar instruments with improved designs which give the surgeon increased stability during endoscopic procedures and improved access to the surgical site.

BACKGROUND OF THE INVENTION

Minimally invasive procedures are desirable over conventional open medical procedures as they reduce pain and provide quick recovery times. Many minimally invasive procedures are performed with an endoscope. Such procedures permit a surgeon to position, manipulate, and view medical instruments and accessories inside the patient through a small access opening in the patient's body.

Arthroscopic surgery is a type of endoscopic surgery in which the intra-articular space is filled with fluid. Arthroscopic surgery is typically enabled by a camera system attached to an endoscope with an angled direction of view. This angled direction of view enables the surgeon to view a more comprehensive image of the anatomy (compared to a "forward looking" scope with a non-angled direction of view) by rotating the arthroscope relative to the camera. Often, this rotation is the only possible manipulation of the scope because the anatomy may prevent other motions (e.g., deflection, pistoning, etc). Rotation of the scope is also the safest manipulation of the scope, with the least potential damage to the surrounding anatomy.

Conventional arthroscopic cameras/arthroscopic systems typically require rotation of the scope by a two-handed operation from the surgeon. For this, the surgeon secures the camera head in one hand and rotates the scope with the other hand by manipulating the light guide attached to the scope. Using two hands for rotating the scope is inconvenient because the surgeons prefer using a therapeutic instrument (such as a shaver or a suture passer, for example) simultaneously with the camera. Thus, the two-handed scope rotation causes delays in surgery.

Some surgeons with large hands are able to rotate the endoscope with one hand, by extending the index finger proximally to rotate the light post (light guide). This is an awkward hand position, however, in which the index finger is unable to apply significant force to rotate the light post. Accordingly, this manipulation often leads to hand fatigue.

An endoscope with an improved ergonomic design that minimizes hand fatigue and increases the efficiency of the endoscopic/arthroscopic procedure is needed. Also needed is a cost effective mechanism that can attach to a conventional endoscope/arthroscope and has a design that allows one-handed endoscope rotation. An ergonomic method for surgeons (with varying hand size) to rotate the endoscope/arthroscope is also needed.

SUMMARY OF THE INVENTION

The present invention provides a rotation mechanism/device that can be easily accessed by the surgeon's finger to rotate an endoscope or similar instrument. The rotation mechanism is a component with a "starfish" configuration, and which can be attached to the endoscope/arthroscope. The starfish component has a plurality of projections (arms) that extend away and radially from the endoscope axis, the projections being easily accessed by the surgeon's finger to rotate the endoscope.

The rotation mechanism may be provided as a unitary component with features for snap fitting onto the endoscope/arthroscope, or may be provided in multiple pieces with fastening devices (for example, screws) for attachment to the arthroscope. The rotation mechanism may be also provided as a reusable (re-sterilizable device) or as a single-use only device.

Other features and advantages of the present invention will become apparent from the following detailed description of the invention, which is provided with reference to the accompanying drawings.

DETAILED DESCRIPTION OF THE INVENTION

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The invention provides rotation mechanisms (rotation devices) that can be easily accessed by the surgeon's finger to rotate an instrument (i.e., an endoscope or similar instrument) and methods of one-handed ergonomic rotation of instruments. The rotation mechanism is a device/component with a "starfish" configuration, and which can be attached to (and detached from) the endoscope. The starfish component has a plurality of projections that extend radially from the endoscope axis, and beyond an outer diameter of a proximal region of the shaft engaged by a surgeon's hand while manipulating the instrument (i.e., an endoscope or similar instrument). Thus, the projections can be easily accessed by the surgeon's finger to rotate the endoscope.

In an exemplary-only embodiment, the rotation mechanism is a device/component with a "starfish" configuration which can be attached to (and optionally detached from) the endoscope just proximally to a means for introducing illumination (for example, a light port or light post) located at the proximal end of the endoscope. The starfish component has a plurality of projections that extend radially from the longitudinal axis of the endoscope to be easily accessed by the surgeon's finger to rotate the endoscope.

In yet another exemplary-only embodiment, the rotation mechanism is a device/component with a "starfish" configuration which can be attached to (and optionally detached from) the endoscope just distally to an eyepiece (or an alternate attachment to a camera) located at the proximal end of the endoscope. The starfish component has a plurality of projections that extend radially from the longitudinal axis of the endoscope to be easily accessed by the surgeon's finger to rotate the endoscope.

In additional embodiments, the rotation mechanism is a device/component with a "starfish" configuration which can be attached to (and optionally detached from) the endoscope at a location between a means for introducing illumination (for example, a light port or light post) of the endoscope and an eyepiece (or an alternate attachment to a camera) of the endoscope. The starfish component has a plurality of projections that extend radially from the endoscope axis, and beyond the outer diameter of the mechanism on the camera head that grasps the arthroscope eyecup. In this manner, the projections can be easily accessed by the surgeon's finger to rotate the endoscope.

The rotation mechanism may be provided as a unitary, single-piece component with features for snap fitting onto the endoscope/arthroscope, or may be provided in multiple pieces with fastening devices (for example, screws) for attachment to the endoscope/arthroscope. The rotation mechanism may be also provided as a reusable (re-sterilizable device) or as a single-use only device.

Although the embodiments below will be explained and detailed with reference to attachment of a rotation mechanism (rotation device) to an arthroscope, the invention is not limited to these exemplary-only embodiments and has applicability to other similar endoscopic instruments such as, for example, videoarthroscopes, laparoscopic devices, colonoscopes, gastroscopes, etc., i.e., to instruments similar to endoscopes/arthroscopes that require manual rotation of the shaft during surgery or surgical intervention, and that permit attachment of the rotation devices of the present invention to the shaft of the instrument.

Figure 1:
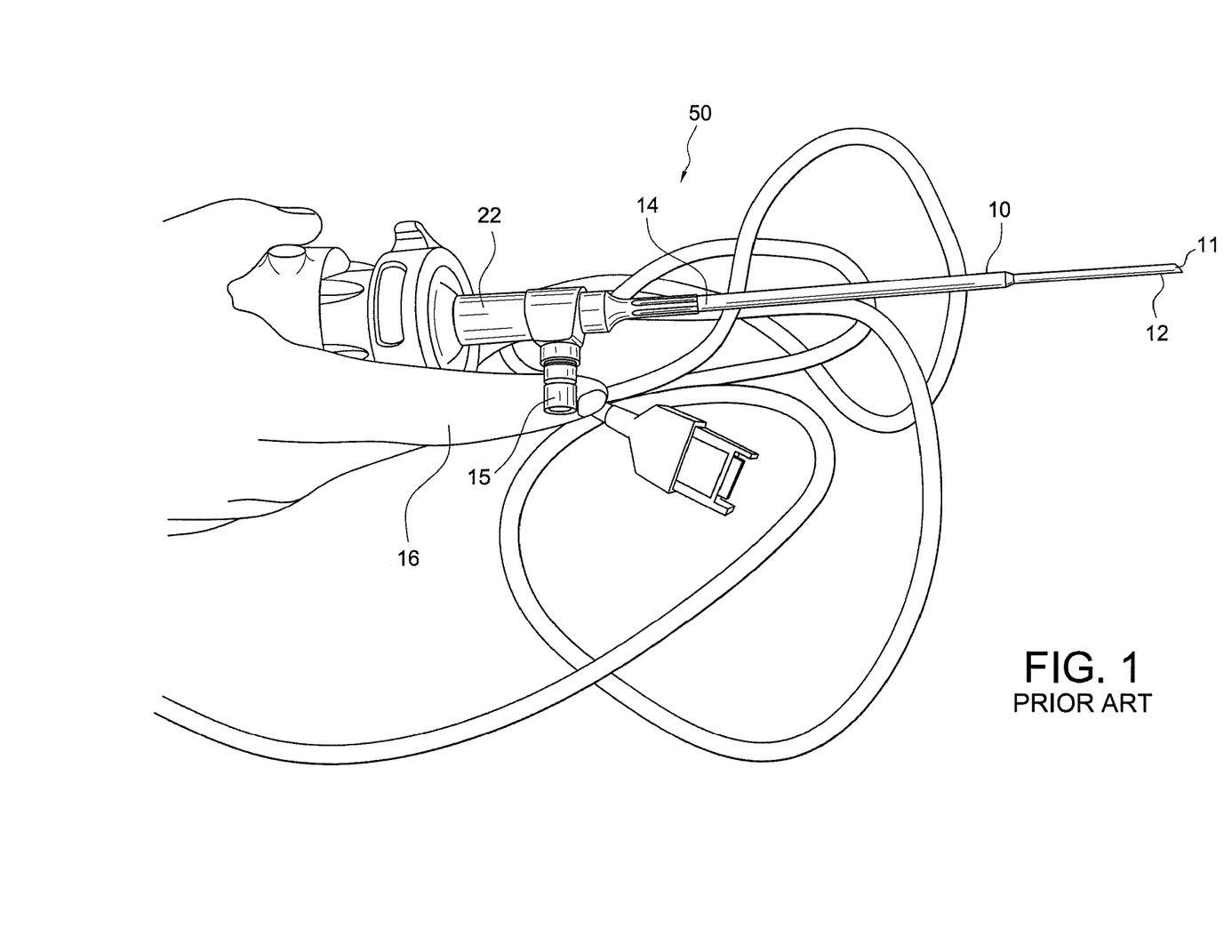
FIG. 1 illustrates a conventional arthroscope installed in a camera head (with which the surgeon has difficulty in reaching the light post (light port) to rotate the endoscope).

Referring now to the drawings, where like elements are designated by like reference numerals, FIG. 1 illustrates an exemplary prior art instrument 50 (arthroscope 50). FIGS. 2-18 illustrate exemplary embodiments of rotation mechanism 100, 100a, 100b, 200 of the present invention designed to be attached (removably or permanently) to an endoscope or similar instrument (such as arthroscope 50 of FIG. 1).

Arthroscope 50 of FIG. 1 is provided with a tubular shaft 10 with a distal end 12 and a proximal end 14, means for introducing illumination 15 in the form of an exemplary light port or post 15 (that houses an optical fiber system or light guiding fiber bundles) and eyepiece 22. Tubular shaft 10 is a hollow, stainless steel tube having a diameter of about 4 mm to about 5.4 mm, housing all optical and illumination components used in basic endoscopic visualization. Tubular shaft 10 houses a lens system that transmits the image from an objective lens 11 to the viewer (surgeon) typically in the form of a relay lens system (in the case of a rigid instrument) or a bundle of fiberoptics (in the case of a fiberscope). Tubular shaft 10 may also include a high resolution imager (e.g., a CCD imager) mounted at the distal end. Tubular shaft 10 may also house at least one working channel (for example, one or more channels for the introduction of instruments, gases or liquids) that extend longitudinally throughout the shaft 10. Exemplary light post 15 is positioned on the side of the handle and carries light from an external light source to the proximal end of the optical fibers and to the viewing end, where the light is emitted to illuminate the region of interest (i.e., the region that is inspected). Arthroscope 50 may further comprise fiber optic bundles, micro processors and cables, as known in the art.

Rotation of arthroscope 50 during surgery typically requires rotation of the arthroscope by a two-handed operation from the surgeon. For this, the surgeon secures the camera head in one hand and rotates the arthroscope 50 with the other hand by manipulating the light guide attached to the light port 15 integral to the arthroscope, i.e., using finger 16 to move the light port 15 (as shown in FIG. 1) and thus rotate the shaft 10 and the camera. Using two hands for rotating arthroscope 50 is inconvenient because the surgeons prefer using a therapeutic instrument (such as a shaver or a suture passer, for example) simultaneously with the camera.

Reference is now made to FIGS. 2-18 which illustrate rotation mechanisms/devices 100, 100a, 100b, 200 of the present invention employed with various instruments such as endoscopes, arthroscopes or similar instruments that require manual rotation of the shaft during surgery or surgical intervention, and that permit attachment of the rotation devices 100, 100a, 100b, 200 of the present invention.

The rotation mechanisms/devices detailed below are devices/components that have a general "starfish" shape or configuration, and that are attached to the exemplary arthroscope 50. In exemplary-only embodiments, the rotation mechanisms/devices may be attached just proximally to a means for introducing illumination (for example, light port or light post 15) located at the proximal end of the endoscope, or may be attached just distally to eyepiece 22 (or an alternate attachment to a camera) located at the proximal end of the endoscope, or at a location between the light post 15 and the eyepiece 22. The rotation mechanisms/devices may be provided as unitary devices (preferably with features for snap fitting onto the shaft of the instrument) or may be provided in multiple pieces (segments) that can be connected with fastening devices (for example, screws) for attachment to the instrument (i.e., endoscope or arthroscope or similar instrument). The rotation mechanisms/devices may be removably or permanently attached to the instrument. Rotation mechanism 100, 100a, 100b, 200 is provided with multiple projections or arms (for example, 6, 8, 10, etc.) that extend radially from the endoscope longitudinal axis.

Figure 2:
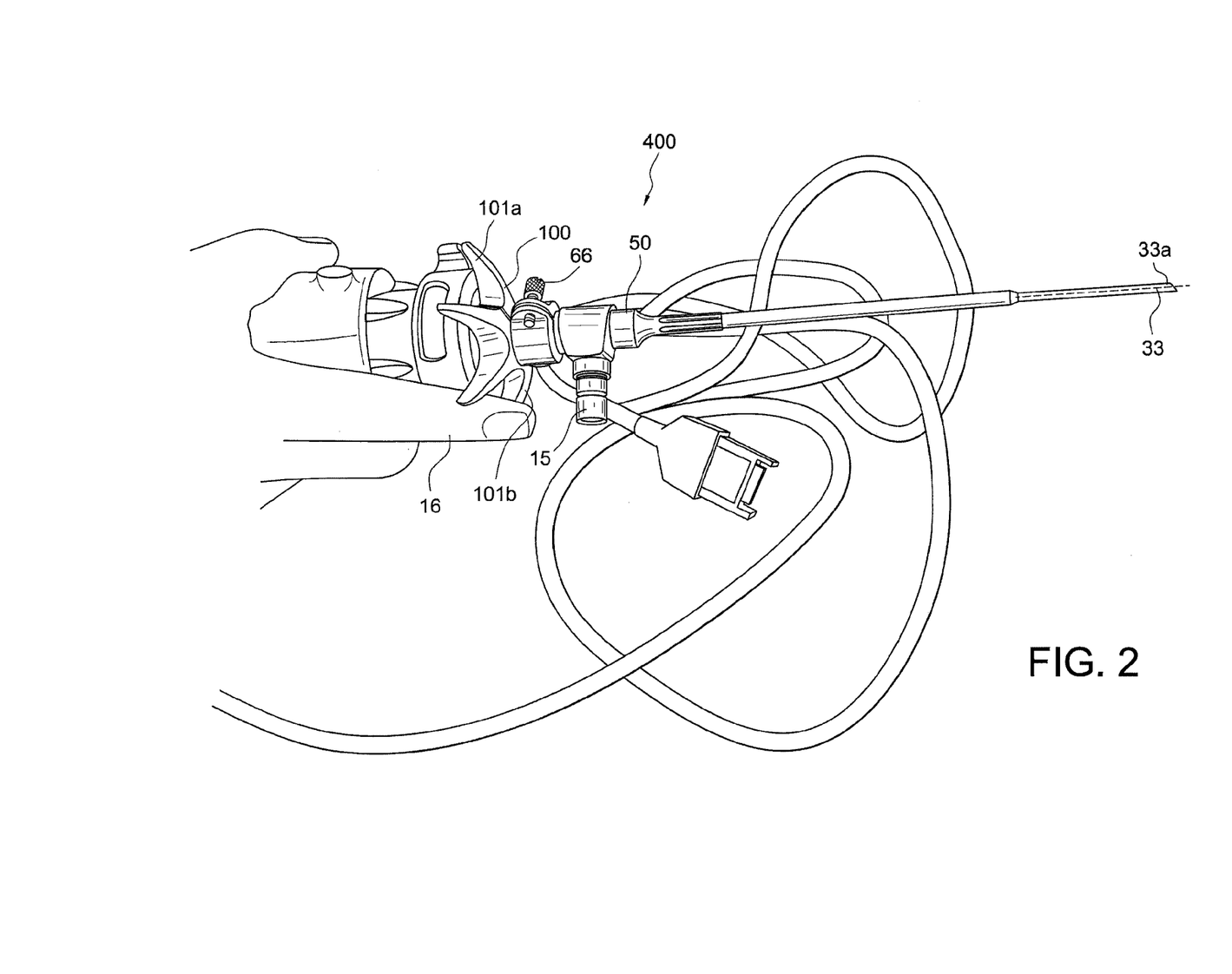
FIG. 2 illustrates a rotation mechanism according to a first exemplary embodiment of the present invention (with 6 projections), and attached to the scope (demonstrating rotation with the index finger).
Figure 3:
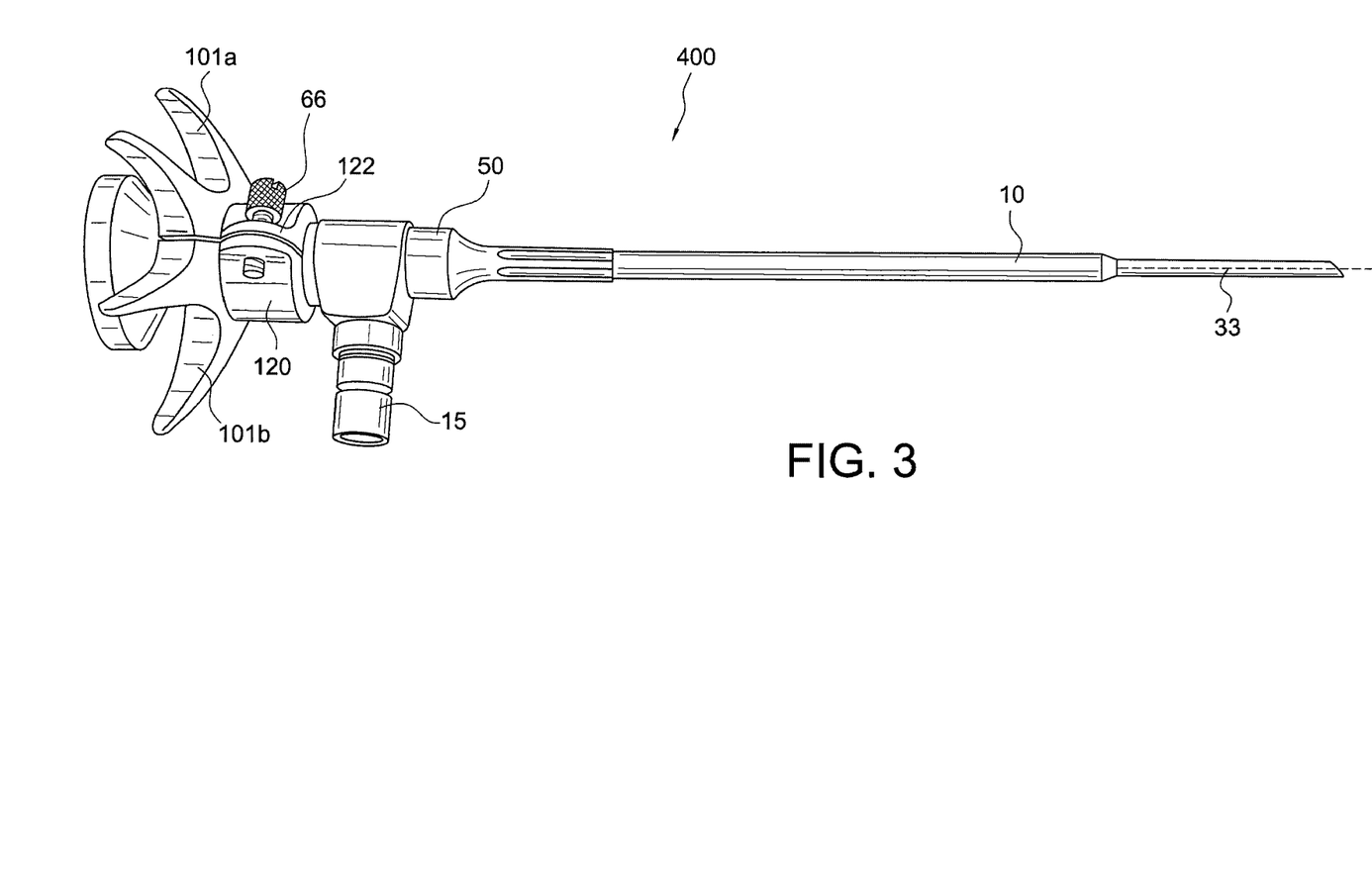
FIG. 3 illustrates another view of the rotation mechanism of FIG. 2, and attached to the scope (but not in camera head).

FIGS. 2-5 illustrate exemplary rotating device/component 100 having a "starfish" shape or configuration with 6 projections (arms). The rotating device/component 100 is attached to arthroscope 50 just proximal to means of introducing illumination 15 (in the form of an exemplary light port or post 15) to form integrated system 400 (FIGS. 2 and 3). Although the light port (post) 15 is shown in FIGS. 2 and 3 as extending about perpendicular to a longitudinal axis 33 (central axis 33) of the shaft of the instrument, the invention is not limited to this exemplary-only embodiment and contemplates posts/ports or similar structures for introducing illumination to the instrument extending in a direction non-parallel to the longitudinal axis 33 of the instrument.

Figure 4:
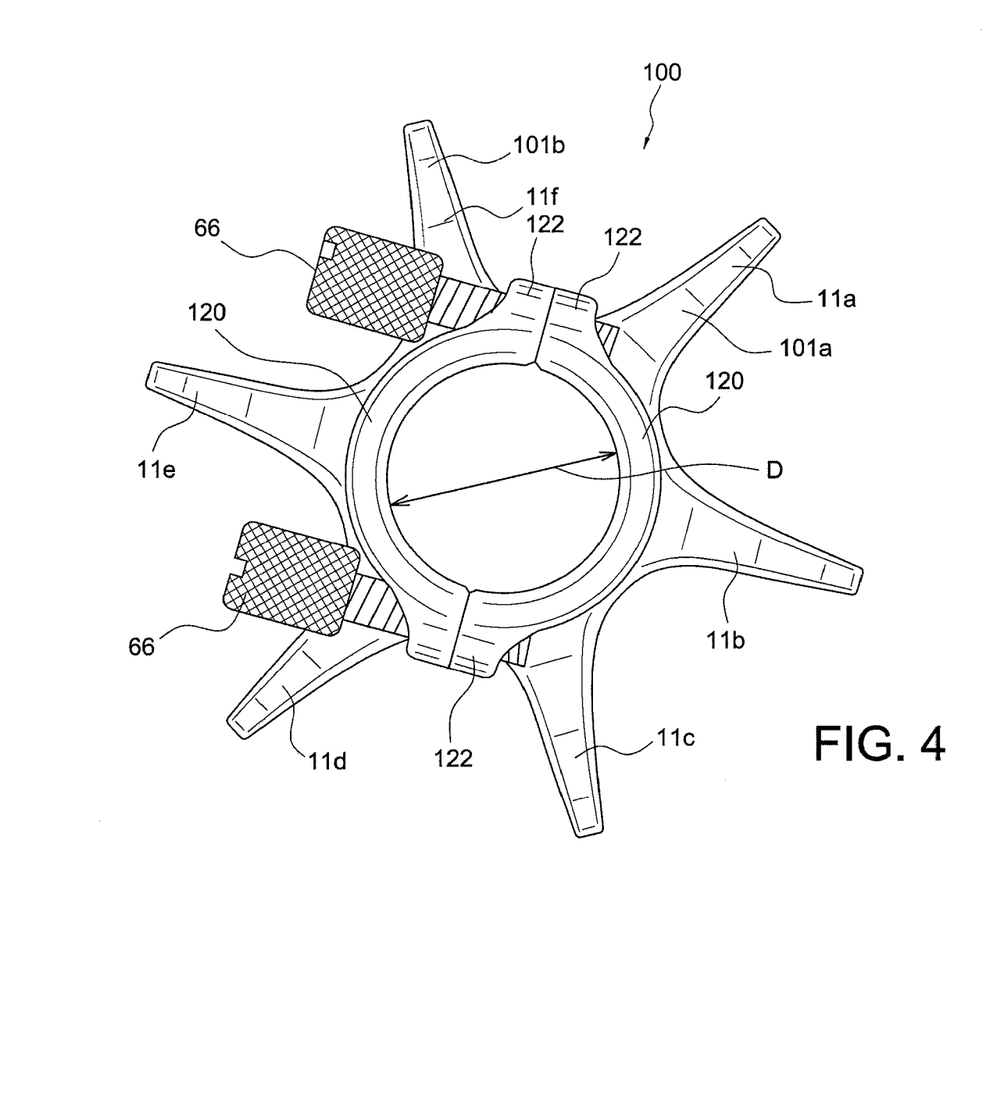
FIG. 4 is a plan view of the rotation mechanism of FIG. 2 (in the assembled state, i.e., with the fastening devices).
Figure 5A:
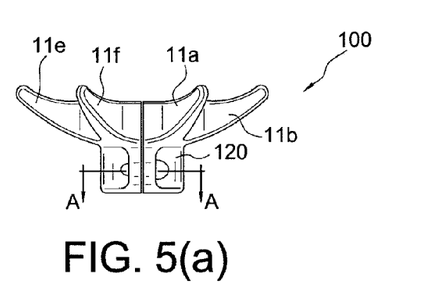
FIG. 5(a) illustrates a schematic front view of the rotation mechanism of FIG. 4 (without the fastening devices).
Figure 5B:
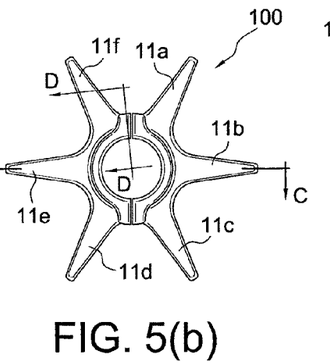
FIG. 5(b) illustrates a top view of the rotation mechanism of FIG. 5(a).
Figure 5C:
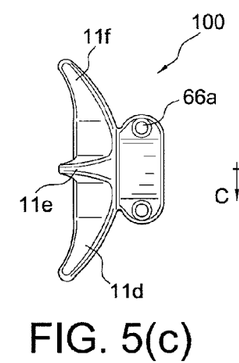
FIG. 5(c) illustrates a left side view of the rotation mechanism of FIG. 5(b).
Figure 5D:
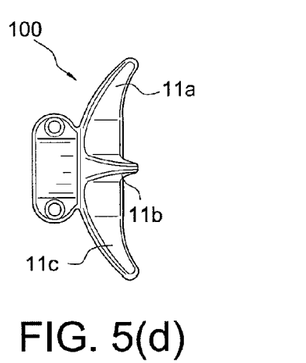
FIG. 5(d) illustrates a right side view of the rotation mechanism of FIG. 5(b).
Figure 5E:
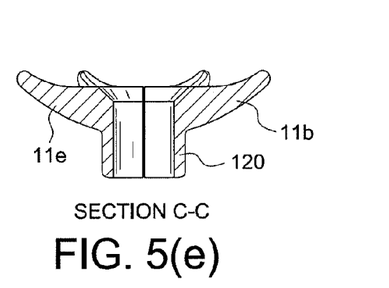
FIG. 5(e) illustrates a cross-sectional view of the rotation mechanism of FIG. 5(b), taken along line C-C of FIG. 5(b).
Figure 5F:
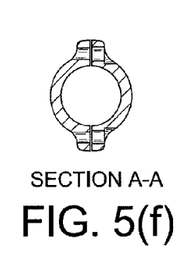
FIG. 5(f) illustrates a cross-sectional view of the rotation mechanism of FIG. 5(a), taken along line A-A of FIG. 5(a).
Figure 5G:
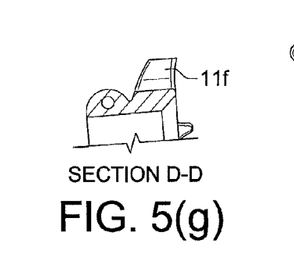
FIG. 5(g) illustrates a partial cross-sectional view of the rotation mechanism of FIG. 5(b), taken along line D-D of FIG. 5(b).
Figure 5H:
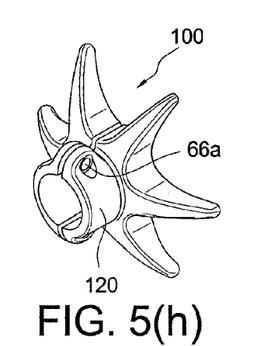
FIG. 5(h) illustrates a perspective view of the rotation mechanism of FIG. 5(a).
Figure 6A:
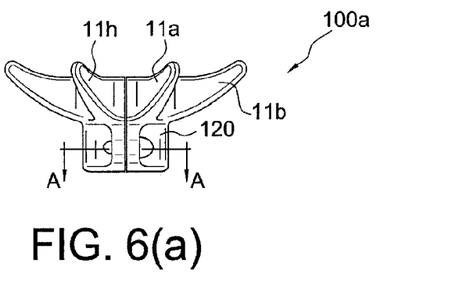
FIG. 6(a) illustrates a schematic front view of a rotation mechanism according to a second embodiment of the present invention (with 8 projections and without the fastening devices).
Figures 6B, 6D:
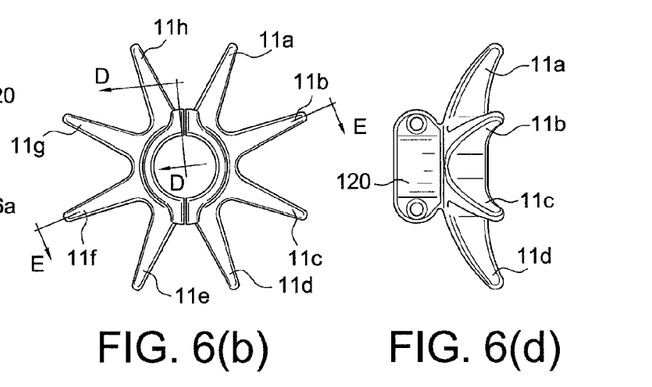
FIG. 6(b) illustrates a top view of the rotation mechanism of FIG. 6(a).
FIG. 6(d) illustrates a right side view of the rotation mechanism of FIG. 6(b).
Figure 6C:
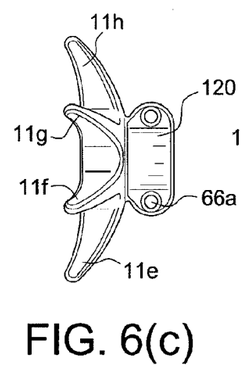
FIG. 6(c) illustrates a left side view of the rotation mechanism of FIG. 6(b).
Figure 6E:
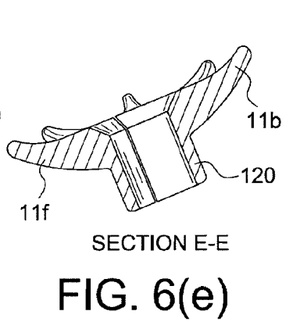
FIG. 6(e) illustrates a cross-sectional view of the rotation mechanism of FIG. 6(b), taken along line E-E of FIG. 6(b).
Figures 6F, 6H:
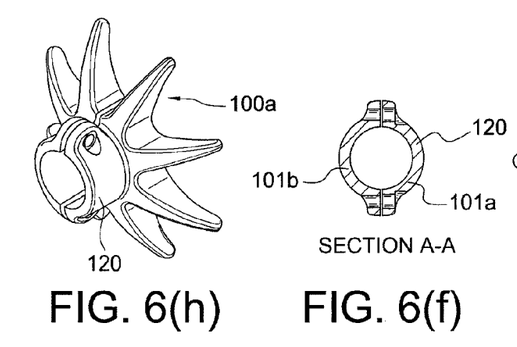
FIG. 6(f) illustrates a cross-sectional view of the rotation mechanism of FIG. 6(a), taken along line A-A of FIG. 6(a).
FIG. 6(h) illustrates a perspective view of the rotation mechanism of FIG. 6(a).
Figure 6G:
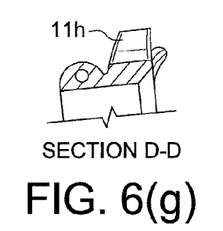
FIG. 6(g) illustrates a partial cross-sectional view of the rotation mechanism of FIG. 6(b), taken along line D-D of FIG. 6(b).
Figure 7A:
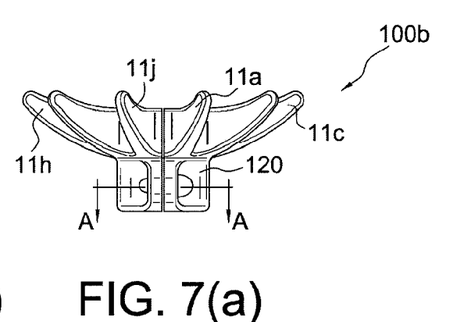
FIG. 7(a) illustrates a schematic front view of the rotation mechanism according to a third embodiment of the present invention (with 10 projections and without the fastening devices).
Figure 7B:
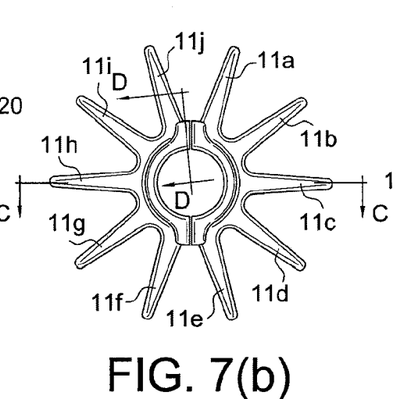
FIG. 7(b) illustrates a top view of the rotation mechanism of FIG. 7(a).
Figure 7C:
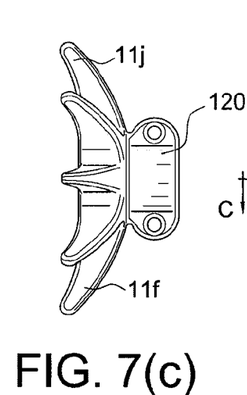
FIG. 7(c) illustrates a left side view of the rotation mechanism of FIG. 7(b).
Figure 7D:
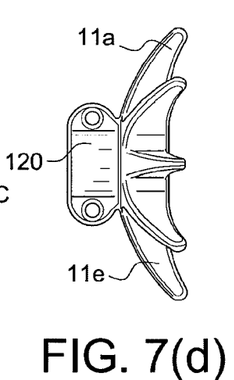
FIG. 7(d) illustrates a right side view of the rotation mechanism of FIG. 7(b).
Figure 7E:
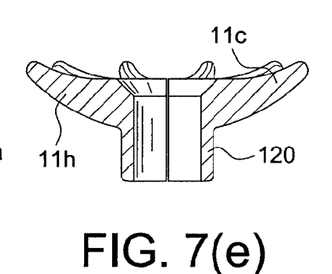
FIG. 7(e) illustrates a cross-sectional view of the rotation mechanism of FIG. 7(b), taken along line C-C of FIG. 7(b).
Figures 7F, 7H:
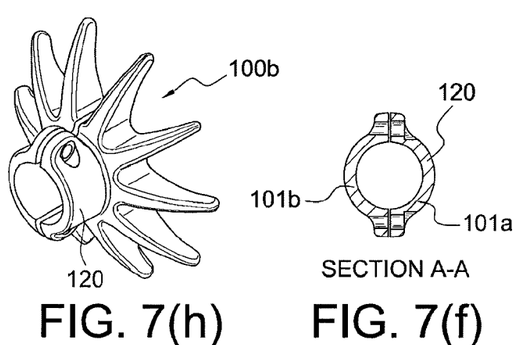
FIG. 7(f) illustrates a cross-sectional view of the rotation mechanism of FIG. 7(a), taken along line A-A of FIG. 7(a).
FIG. 7(h) illustrates a perspective view of the rotation mechanism of FIG. 7(a).
Figure 7G:
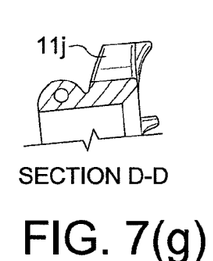
FIG. 7(g) illustrates a partial cross-sectional view of the rotation mechanism of FIG. 7(b), taken along line D-D of FIG. 7(b).
Figures 8, 9:
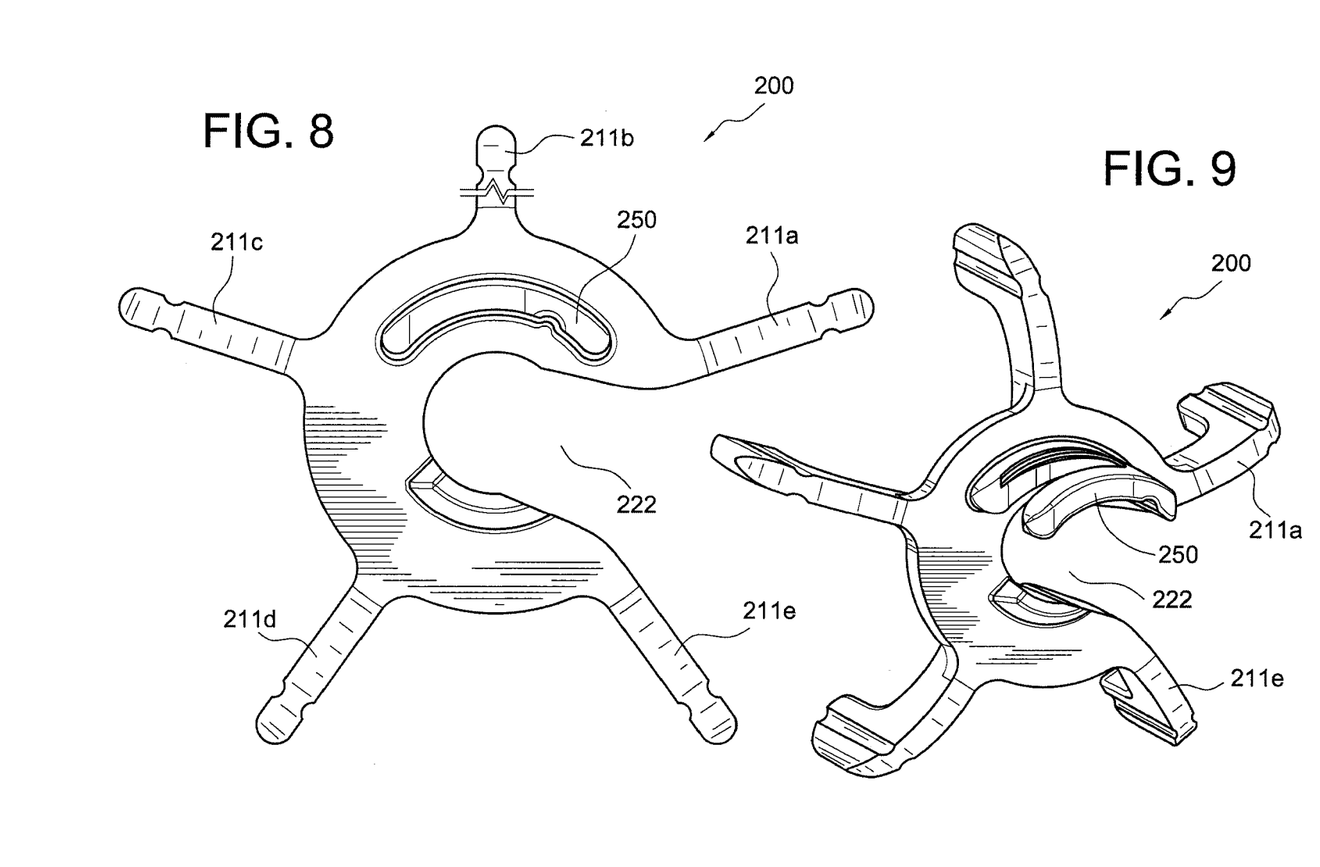
FIG. 8 illustrates a top view of a rotation mechanism according to another exemplary embodiment of the present invention (a single-piece, unitary device that snap fits onto the shaft).
FIG. 9 illustrates a perspective view of the rotation mechanism of FIG. 8.
Figure 10A:
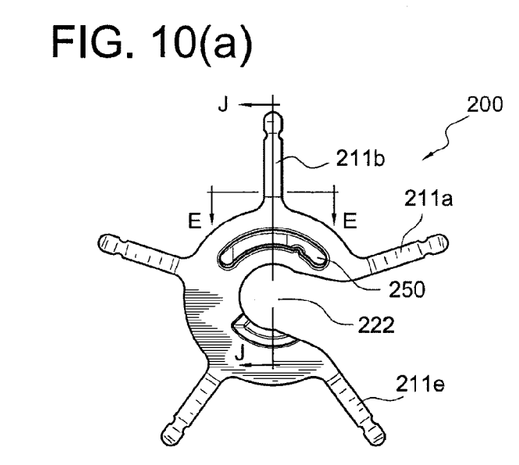
FIG. 10(a) illustrates another top view of the rotation mechanism of FIG. 8.
Figure 10B:
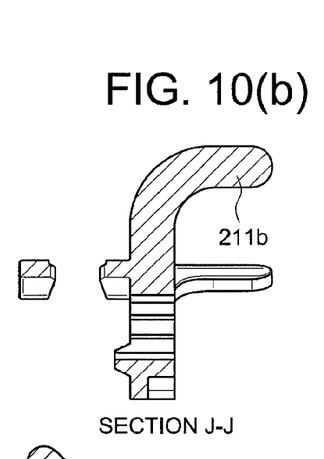
FIG. 10(b) illustrates a cross-sectional view of the rotation mechanism of FIG. 10(a), taken along line J-J of FIG. 10(a).
Figure 10C:
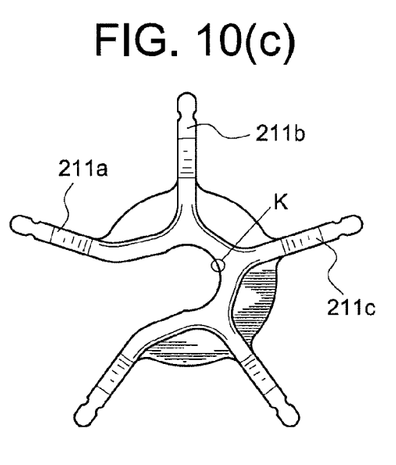
FIG. 10(c) illustrates a bottom view of the rotation mechanism of FIG. 10(a).
Figure 10D:
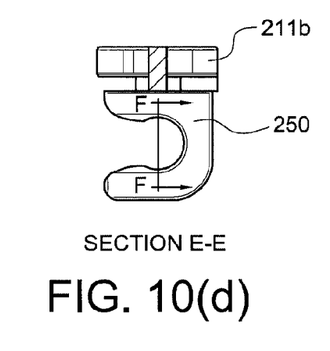
FIG. 10(d) illustrates a cross-sectional view of the rotation mechanism of FIG. 10(a), taken along line E-E of FIG. 10(a).
Figure 10E:
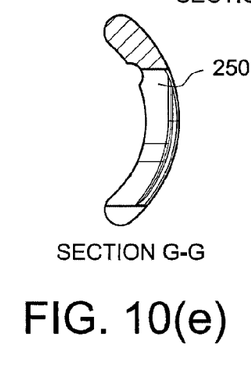
FIG. 10(e) illustrates a cross-sectional view of the rotation mechanism of FIG. 10(f), taken along line G-G of FIG. 10(f).
Figure 10F:
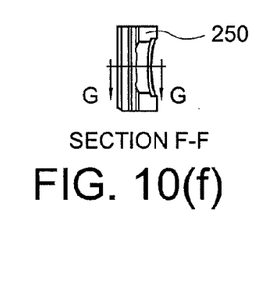
FIG. 10(f) illustrates a cross-sectional view of the rotation mechanism of FIG. 10(d), taken along line F-F of FIG. 10(d).
Figure 10G:
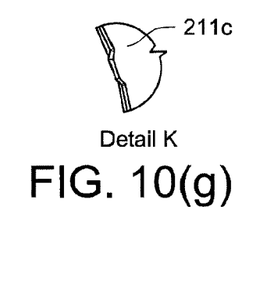
FIG. 10(g) illustrates detail K of the rotation mechanism of FIG. 10(c).
Figure 11:
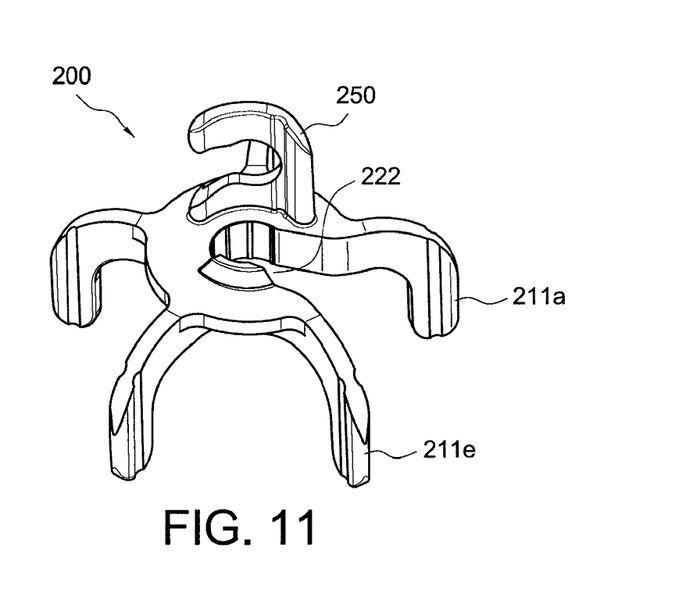
FIGS. 11-15 illustrate additional views of the rotation mechanism of FIG. 8.
Figure 12:
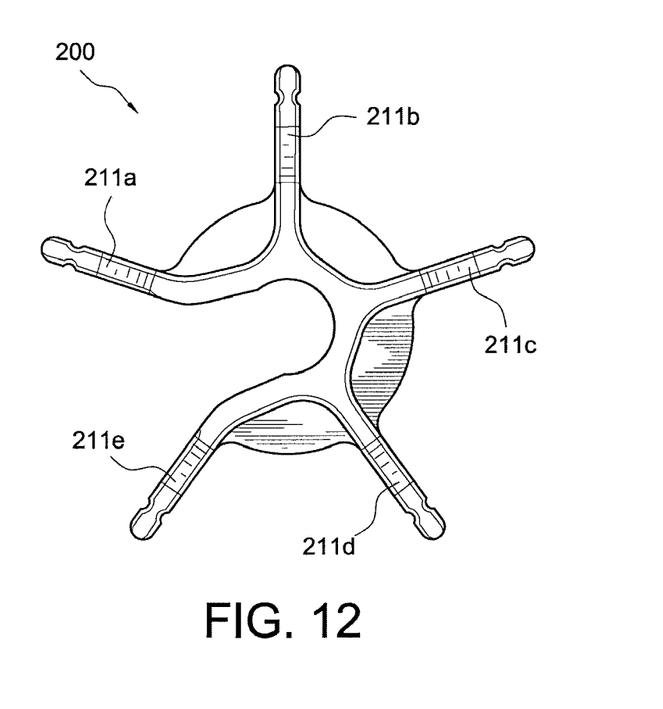
Figure 13:
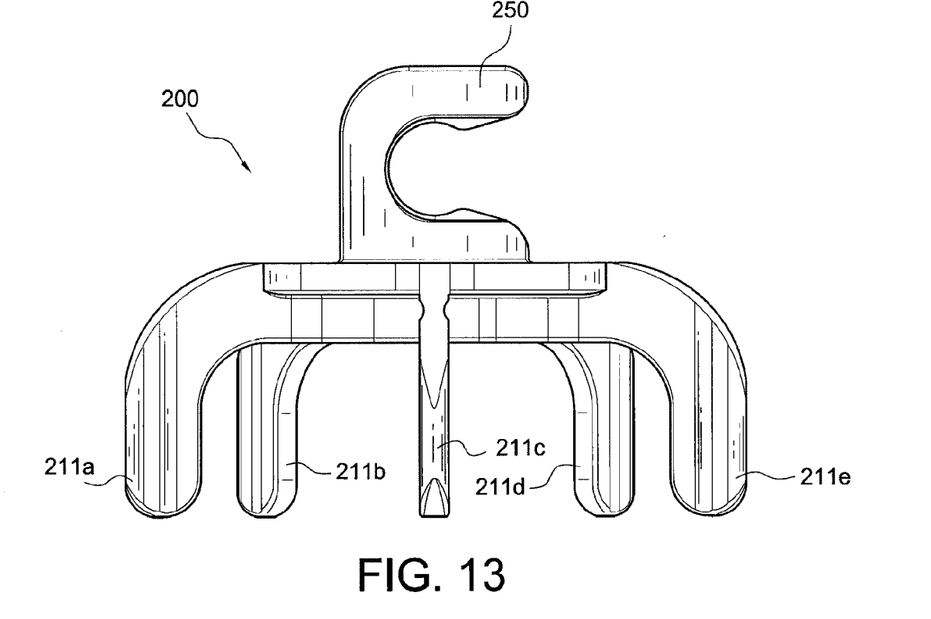
Figure 14:
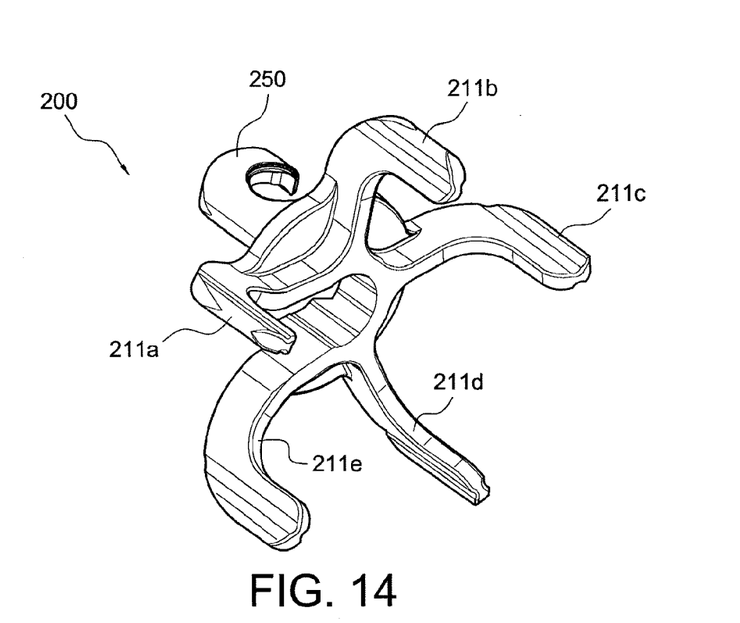
Figure 15:
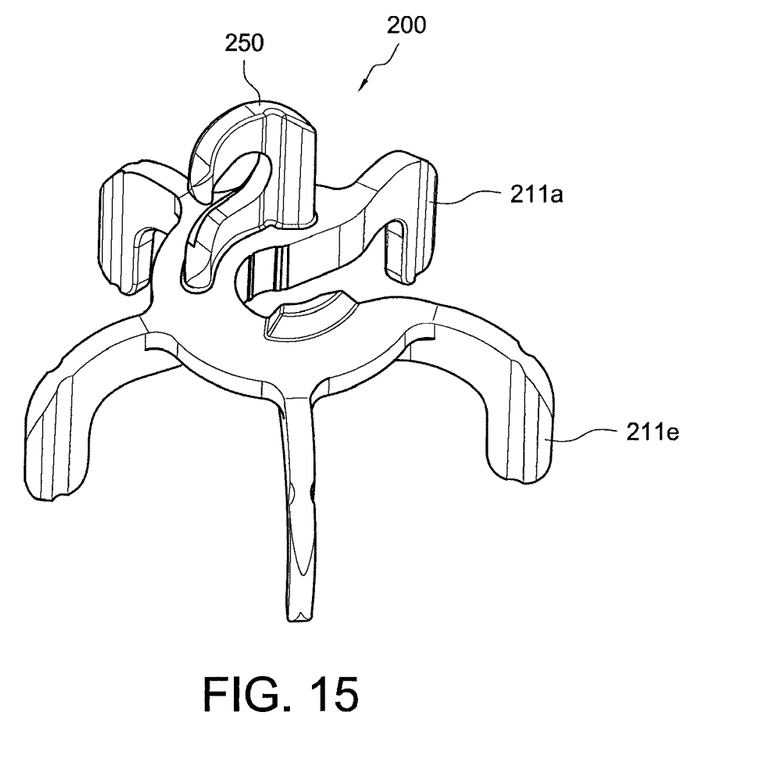

The exemplary embodiment shown in FIGS. 4 and 5 depicts component 100 with 6 projections 11a-11f extending radially and outwardly from the endoscope central axis 33, and also located symmetrically relative to the central axis 33 and to each other. In the assembled state, rotating device/component 100 is also provided with a neck region in the form of a tubular section or cylinder 120 with flanges 122 or clamps 122 (FIG. 4) having holes that allow fixation devices to pass through and secure segments of the rotating device together, and to the shaft of the instrument. The inner diameter D of tubular section 120 is about equal to the outer diameter of the proximal section of the shaft region just proximal to the light port 15, to allow secure engagement and coupling of the rotating device/component 100 to the proximal section of the shaft 10 (proximally to the light post 15).

In an exemplary and illustrative embodiment only, rotating device/component 100 is divided into (formed of) two symmetric halves 101a, 101b (two symmetrical segments 101a, 101b) with eyelets/through holes 66a that receive fastening devices 66 (for example, locking means such as two screws 66, or other similar devices such as adhesives and/or fixation devices). The halves 101a, 101b attach to each other and are applied to the cylindrical area at a location just distally to the eyepiece flange. The screws 66 secure the mechanism. The components can be removed for sterilization and cleaning.

FIG. 4 shows the rotating device/component 100 in the assembled form. FIGS. 5(a)-5(h) show details of segments 101a, 101b of the rotating device/component 100 in the unassembled form (i.e., with the fasteners removed). Once assembled (fastened), the two symmetrical halves or segments 101a, 101b form the tubular section 120 with flanges 122 having through holes 66a secured to each other by fastening devices 66.

Exemplary projections 11a-11f of rotation mechanism 100 extend radially beyond the outer diameter of the mechanism on the camera head. In this manner, during use of the instrument 50, the projections 11a-11f can be easily accessed by the surgeon's finger 16 to move (push) the projection and to rotate, therefore, the instrument (as shown in FIG. 2). Projections 11a-11f may have a general triangular configuration (as shown in FIG. 4) but the invention is not limited to this exemplary-only embodiment and contemplates other geometries and configurations of the projections, as long as they are easily reachable by operators even with small hands, to be rotated with the index finger.

FIGS. 6(a)-6(h) illustrate various views of rotation mechanism 100a (Starfish 100a) according to a second exemplary embodiment of the present invention (with 8 projections 11a-11h). This embodiment is similar to rotation mechanism/device 100 of FIGS. 2-5 but differs from it only in the number of projections (arms) extending radially from the instrument (i.e., 8 projections in lieu of 6 projections).

FIGS. 7(a)-7(h) illustrate various views of rotation mechanism 100b according to a third exemplary embodiment of the present invention (with 10 projections 11a-11j). This embodiment is similar to rotation mechanism/device 100, 100a of FIGS. 2-6 but differs from them only in the number of projections (arms) extending radially from the instrument (i.e., 10 projections in lieu of 6 or 8 projections). Exemplary projections 11a-11j of rotation mechanism 100, 100a, 100b extend radially beyond the diameter of the mechanism on the camera head. During use of the instrument, the projections can be easily accessed by the surgeon's finger to rotate the instrument.

Compared to rotating a conventional scope 50 with the light post 15 (shown in FIG. 1), the rotating mechanism 100, 100a, 100b of the present invention provides the following advantages:

the projections are more proximal, enabling one-hand rotation for surgeons with smaller hands;

the projections are more proximal, enabling more ergonomic rotation with the index finger; and there are multiple projections (compared to just one light post) enabling the same hand motion to rotate the endoscope, regardless of the light post position.

Alternate embodiments of the manual rotating mechanism/device contemplated by the present invention include at least one of the following features:

the mechanism projections are permanently attached to the endoscope;

the projections are fabricated as part of the endoscope eyepiece (i.e., not a separate component);

the mechanism can include a hinge on one side, eliminating one fixation device (screw) and facilitating installation and removal;

the mechanism can be fabricated from a polymeric material with features for "snap fitting" onto the endoscope, eliminating both screws and facilitating installation and removal;

the mechanism can be either a one-time-use device (polymeric material for cost effective manufacturing) or re-sterilizable (either aluminum, or sterilizable polymer (e.g. PEEK)).

For example, FIGS. 8-18 illustrate yet another embodiment of the present invention according to which rotating mechanism/device 200 is a single-piece, low-cost device (construct) formed as a unitary piece that eliminates the need for fastening devices (such as fastening devices 66) and facilitates installation and removal of the device onto and from the shaft of the instrument (i.e., endoscope, arthroscope or similar instrument). Rotating mechanism/device 200 can be fabricated from a polymeric material with features for "snap fitting" onto the endoscope. Device 200 may be formed by machining or molding (for example, injection molding or insert molding), or by any known methods of the art. By enabling molding, the device may be sold as a single-use, disposable construct in lieu of a sterilizable construct.

As in the previous embodiments, rotating mechanism/device 200 also includes a plurality of arms 211a-211e (projections 211a-211e) extending radially from the endoscope axis, and beyond the diameter of the mechanism on the camera head that grasps the arthroscope eyecup. As in the previously-detailed embodiments, the projections 211a-211e can be also easily accessed by the surgeon's finger to rotate the endoscope. Rotating mechanism/device 200 includes, however, attachment 250 (in the form of a partial, molded ring or collet 250) that engages and snaps onto the light post 15 (light guide 15 that houses the light guiding fiber bundles or an optic fiber system) as more clearly shown in FIGS. 16-18, to form integrated system 500. Molded partial ring 250 (collet 250) has an opening that allows the light post 15 to be secured therein and engaged by the rotating mechanism/device 200. Rotating mechanism/device 200 also includes an opening 222 with dimensions configured to receive the shaft of the instrument (i.e., to allow the device to securely engage the shaft of the instrument when the rotating mechanism is snap-fitted onto it) and to otherwise removably mate with proximal end 14 of the instrument (adjacent and proximal to the light post 15, and positioned between the light post 15 and the eyecup 22). The eyecup 22 (eyepiece 22) is located at the most proximal portion of the telescope and it is commonly used as a video camera mount.

Figures 16, 17, 18:
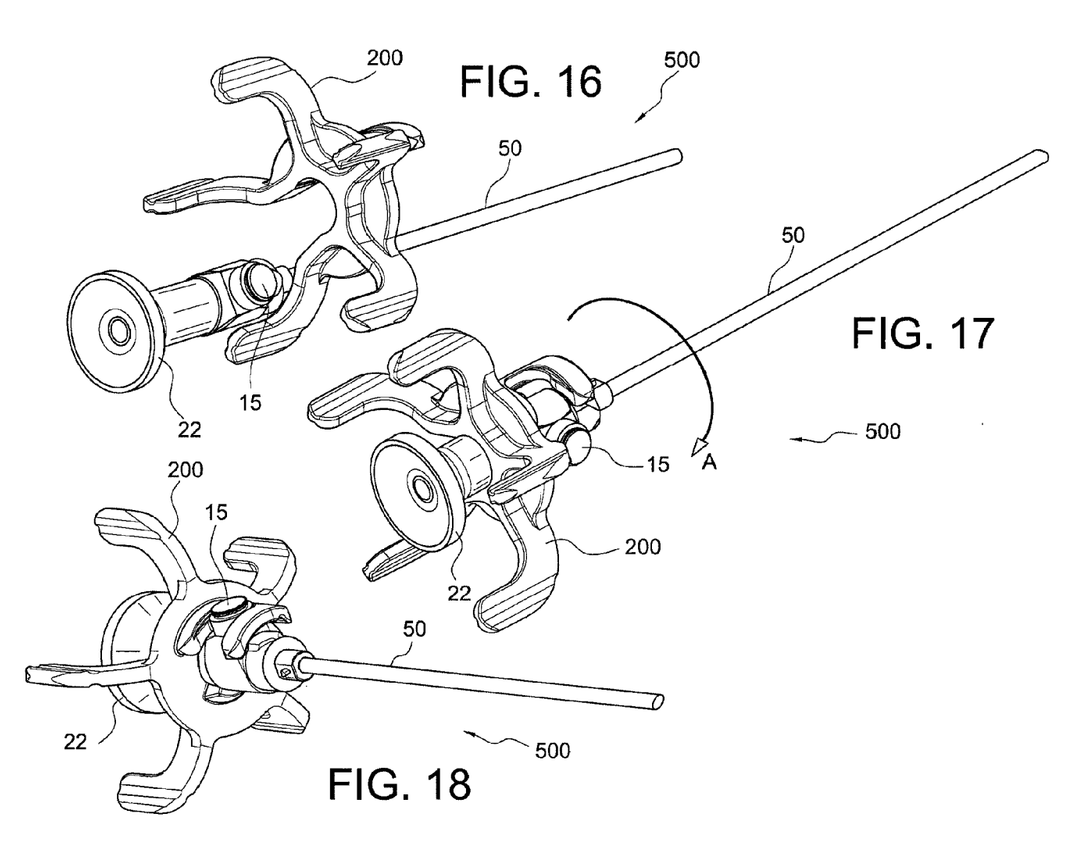
FIGS. 16-18 illustrate subsequent steps of a method of assembling (attaching) the rotation mechanism of FIG. 8 to an exemplary instrument (for example, an arthroscope).

When the rotating mechanism/device 200 is pushed together and snap-fitted with the instrument (for example, with arthroscope 50 of FIG. 1, and as shown in FIG. 16), the rotating mechanism/device 200 is rotated (in the direction of arrow "A" of FIG. 17) and snap-fitted so that attachment 250 securely engages (wraps around) the light post 15 (light guide 15), as shown in FIG. 18. In this manner, actuating one of the arms/projections 211a-211e with finger 16 (by manually pushing to the left or right one of the arms/projections 211a-211e) allows the light post 15 to rotate which in turn rotates the shaft of the instrument, i.e., rotates the instrument (endoscope, arthroscope or similar instrument) relative to the camera. Preferably, system 500 of the present invention uses a 30, 45 or 70 optical system, allowing the practitioner (surgeon) to have improved access to pathology in the joint.

The rotating mechanism 100, 100a, 100b, 200 (starfish 100, 100a, 100b, 200) described above is a cost effective device that can be attached to typical endoscopes/arthroscopes or similar instruments (manufactured in high volume and therefore more cost-effective) to enable one-handed scope rotation. The improved ergonomic design minimizes hand fatigue and increases the efficiency of the arthroscopic procedure.

A method of one-hand only rotation of an endoscope or similar instrument with the manual rotation device 100, 100a, 100b, 200 of the present invention comprises the steps of: (i) securing rotation device 100, 100a, 100b, 200 to a shaft 10 of an endoscope 50, the rotation device 100, 100a, 100b, 200 comprising a plurality of arms 11a-11j, 211a-211e that extend radially from a longitudinal axis of the shaft 10 and beyond a diameter of a mechanism on a camera head that grasps an endoscope eyecup 22, the rotation device being provided distally to the eyepiece 22 (or an alternate attachment to a camera), and optionally between a light post 15 (or similar means for introducing illumination) and the eyepiece; and (ii) manually actuating at least one of the plurality of projections 11a-11j, 211a-211e to rotate the shaft relative to the camera.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. An endoscope, comprising:

a shaft comprising a longitudinal axis, a proximal end and a distal end; and a rotating device attached to the shaft and snap-fitted onto the endoscope, the rotating device comprising a plurality of arms that extend radially from the longitudinal axis of the shaft and that are actuated by an operator's finger to rotate the rotating device and the shaft, the rotating device further comprising an attachment device configured to engage and snap onto a portion of the endoscope, the rotating device further comprising an opening with dimensions configured to receive the shaft of the endoscope and securely engage the shaft when the rotating device is snap-fitted onto the endoscope;

wherein the endoscope further comprises a port located at the proximal end of the shaft and extending away from the shaft and in a direction non-parallel to the longitudinal axis of the shaft, and an eyepiece or attachment to a camera, the eyepiece or the attachment to the camera being located proximally to the port, and wherein the rotating device is provided between the port and the eyepiece or the attachment to the camera;

wherein the port is a light port and wherein the plurality of arms of the rotating device extend radially beyond an outer diameter of the eyepiece or the attachment to the camera to allow access by an operator's finger to rotate the rotating device and the shaft; and wherein the attachment device of the rotating device further comprises a collet that is configured to snap-fit onto the light port.

2. The endoscope of claim 1, wherein the rotating device is manually actuated by pushing one of the plurality of arms to rotate the endoscope and to orient elements at the distal end of the endoscope in a desired position.

3. The endoscope of claim 1, wherein the rotating device is a single-use disposable device.

4. The endoscope of claim 1, wherein the rotating device is removably attached to the shaft.

5. In an endoscope system, an improvement for rotating the endoscope to allow an operator to orient elements at the distal end of the endoscope in desired positions, wherein the improvement comprises: a rotating device removably attached to a shaft of the endoscope, the rotating device comprising a tubular body and plurality of projections extending radially from a longitudinal axis of the shaft, the plurality of projections having a starfish configuration and being integral with the tubular body, the projections being configured to be manually actuated by the operator, with a single finger, to effect rotation of the shaft;

wherein the rotating device is a component designed to snap-fit onto the shaft, at a location between a means for introducing illumination and an eyepiece or an alternate attachment to a camera of the endoscope, wherein the means for introducing illumination extends radially from the longitudinal axis of the shaft and in a direction non-parallel to the longitudinal axis of the shaft, and wherein the eyepiece or the alternate attachment to a camera extends in a direction along the longitudinal axis of the shaft;

wherein the means for introducing illumination is a light post; and wherein the rotating device is molded component further comprising a collet designed to snap-fit proximally to the light post.

* * * * *